United States Patent [19]

Crawford et al.

[11] Patent Number: 4,626,991
[45] Date of Patent: Dec. 2, 1986

[54] SYSTEM FOR REPROJECTING IMAGES ACQUIRED BY BACKPROJECTION

[75] Inventors: Carl R. Crawford, Haifa; Asher Reuveni, Natanya, both of Israel

[73] Assignee: Elscint Incorporated, Boston, Mass.

[21] Appl. No.: 487,310

[22] Filed: Apr. 21, 1983

[51] Int. Cl.[4] .............................................. G06F 15/42
[52] U.S. Cl. ...................................... 364/414; 378/4; 378/901; 358/111
[58] Field of Search ................................ 364/413–414, 364/570–572; 378/4, 14, 18–20, 901; 358/111; 382/6, 54

[56] References Cited

U.S. PATENT DOCUMENTS

| 4,217,641 | 8/1980 | Naparstek | 364/414 |
| 4,219,876 | 8/1980 | Mizutani et al. | 364/414 |
| 4,222,104 | 9/1980 | Moore | 364/414 |
| 4,223,384 | 9/1980 | Hounsfield et al. | 364/414 |
| 4,241,404 | 12/1980 | Lux | 364/414 |
| 4,422,146 | 12/1983 | Yamaguchi et al. | 364/414 |
| 4,442,489 | 4/1984 | Wagner | 364/414 |
| 4,458,358 | 7/1984 | Klausz | 378/19 |
| 4,472,823 | 9/1984 | Waltham | 378/19 |
| 4,476,497 | 10/1984 | Oshikoshi et al. | 358/111 X |
| 4,482,958 | 11/1984 | Nakayama et al. | 364/414 |

OTHER PUBLICATIONS

Stonestrom, J. Peter, et al., "A Framework for Spectral Artifact Corrections in X-Ray CT", IEEE Transactions on Biomedical Engineering, vol. BME-28, No 2, Feb. 1981, pp. 128-141.
Glover, G. H., et al., "An Algorithm for the Reduction of Metal Clip Artifacts in CT Reconstruction", Medical Physics, vol. 8, No. 6, Nov. 1981, pp. 799-807.
Henrich, G., "A Simple Computational Method of Reducing Streak Artifacts in CT Images", Computed Tomography, vol. 4, 1981, pp. 67-71.
Peters, T. M., "Algorithms for Fast Back- and Re-Projection in Computed Tomography", IEEE Transactions on Nuclear Science, vol. NS-28, No. 4, Aug. 1981, pp. 3641-3647.

Primary Examiner—Gary V. Harkcom
Attorney, Agent, or Firm—Sandler & Greenblum

[57] ABSTRACT

A system and method are presented for reprojecting images generated by a back-projector. The image data is processed to distinguish hard and soft tissue and then is transmitted to the normal input of the back-projector. Pseudo-projections (reprojections) are obtained at the normal output of the back-projector. Each image row is fed into the input of the back-projector as a normal projection. The "image" generated by the back-projector is now one projection. In order to generate the required amount of reprojections "L", the image is supplied to the back-projector "L" times. Each time the image is presented with constants, such as the reprojection angle associated with the specific reprojection. The reprojections at the back-projector output are combined in a feed-back circuit with the original projections to correct for artifacts, such as polychromatic artifacts.

9 Claims, 3 Drawing Figures

SYSTEM FOR REPROJECTING IMAGES ACQUIRED BY BACKPROJECTION

FIELD OF THE INVENTION

This invention is concerned with computer generated images and more particularly with systems for reprojecting such images for artifact correction or other purposes.

BACKGROUND OF THE INVENTION

The evolution of x-ray computed tomography (CT) has produced scanners with decreasing data acquisition and image reconstruction times and increasing density and spatial resolutions. The improvements have been achieved primarily by the use of more sophisticated data acquisition systems and faster image reconstruction hardware. A second means for improving the image quality has been to reevaluate assumptions made in order to build the early generations of CT scanners and to incorporate corrections within the image reconstruction algorithm. These assumptions were made in order for the data collected by an actual scanner to be compatible with theoreitcal reconstruction algorithms.

An example of these engineering assumptions has to do with the spectrum of the x-ray source and the energy dependence of the attenuation coefficients of different elements of the object under examination. An important assumption used in the past to produce images is that the source is monochromatic or that the energy dependence of the attenuation coefficients is identical for all elements. It is well known that neither of these two conditions is satisfied and hence what is known as polychromatic artifacts are produced in resulting images. The artifacts can be identified as cupping and as negative streaks between sharp objects that have high attenuation coefficients.

The prior art, see for example U.S. Pat. No. 4,217,641, uses an iterative post-reconstruction method to reduce the level of polychromatic artifacts. Among other known prior art describing polychromatic artifact correction techniques are: U.S. Pat. Nos. 4,222,104 and 4,223,384 as well as an article entitled "A Framework for Spectral Artifact Corrections in X-ray Computed Tomography," by J. Peter Stonestrom, et. al., in the IEEE Transactions on Biomedical Engineering, Vol. BME-28, No. 2, February 1981.

The basis of these prior art post-reconstruction correction methods is that objects are made up of two approximately homogeneous components with respect to the energy dependence of their attenuation coefficients. In biological applications the two components are bone and soft tissue. An initial image is reconstructed incorporating first-order polychromatic corrections for the majority element, usually soft tissue. The initial image is then segmented on a pixel-by-pixel basis in order to generate approximate images of the two components. The path lengths are then calculated through the two images using reprojection techniques. Error projections are then formed from the reprojections and added to the projection data that was used to form the initial image. A second-order image is then reconstructed from the new projection data. If the level of polychromatic correction is sufficient, then the algorithm is complete. If not, the above procedure is repeated.

The use of reprojection is not limited to polychromatic correction algorithms. The paper "An Algorithm for the Reduction of Metal Clip Artifacts in CT Reconstructions," by G. H. Glover and N. J. Pelc, in Medical Physics, Vol. 8, No. 6, November 1981, presents a method to remove the artifacts caused by metal clips using reprojejction as part of their algorithm. The paper "A Simple Computational Method for Reducing Streak Artifacts in CT Images," by G. Henrich, in Computed Tomography, Vol. 4, 1981, describes an algorithm that can be used to remove streaks such as those caused by partial volume artifacts.

The polychromtic-, metal clip-, and streak-artifact correction algorithms described in the prior art have not been implemented commercially because the reprojection step has been extremely time-consuming. The prior art reprojection methods have been too slow because they have relied upon the inherent reprojection step incorporated in the reconstruction algorithms based on algebraic techniques. The slowness of the prior art reprojection systems and an attempted solution are highlighted in a paper "Algorithms for Fast Back- and Re-projection in Computed Tomography," by T. M. Peters, in IEEE Transactions on Nuclear Science, Vol. NS-28, No. 4, August 1981. The paper presents a method that uses a modified backprojector to obtain reprojections. The problem with this system is that the modifications radically change the hardware of a backprojector and thus the system is not readily applicable to commercially installed CT units. The system requires means to reverse the normal data flow through the backprojector, resulting in reprojections at the normal input of the unit. In addition to the need for changed hardware, the resulting reprojections are of poor quality and require complex corrections in order to use them with an artifact correction algorithm.

Accordingly there is a long-standing need for fast reprojection techniques and equipment.

BRIEF DESCRIPTION OF THE INVENTION

According to a preferred embodiment of the invention, a system for reprojecting images acquired by backprojection is provided; said system comprising:
means for converting radiation passing through a subject to electrical signals which are a function of the attenuation in the path of the radiation through the subject,
means for preprocessing said signals,
means for filtering said preprocessed signals,
means for backprojecting said filtered preprocessed signals to provide digitized images of the subject, and
means including the backprojecting means for reprojecting the image of the subject by passing the image to the normal input of the backprojector and obtaining reprojections at the normal output.

A feature of the invention is the use of the reprojected values for correcting polychromatic artifacts.

The required polychromatic correction method is accomplished by using the unmodified backprojection system as a reprojector in order to obtain reprojections in a time comparable to the backprojection time thereby enabling the implementation of a commercially viable polychromatic correction system.

BRIEF DESCRIPTION OF THE DRAWINGS

The above mentioned and other objects and features of the invention will be better understood in conjunction with the following description of the invention taken in conjunction with the accompanying drawings, wherein.

GENERAL DESCRIPTION

Figure 1:
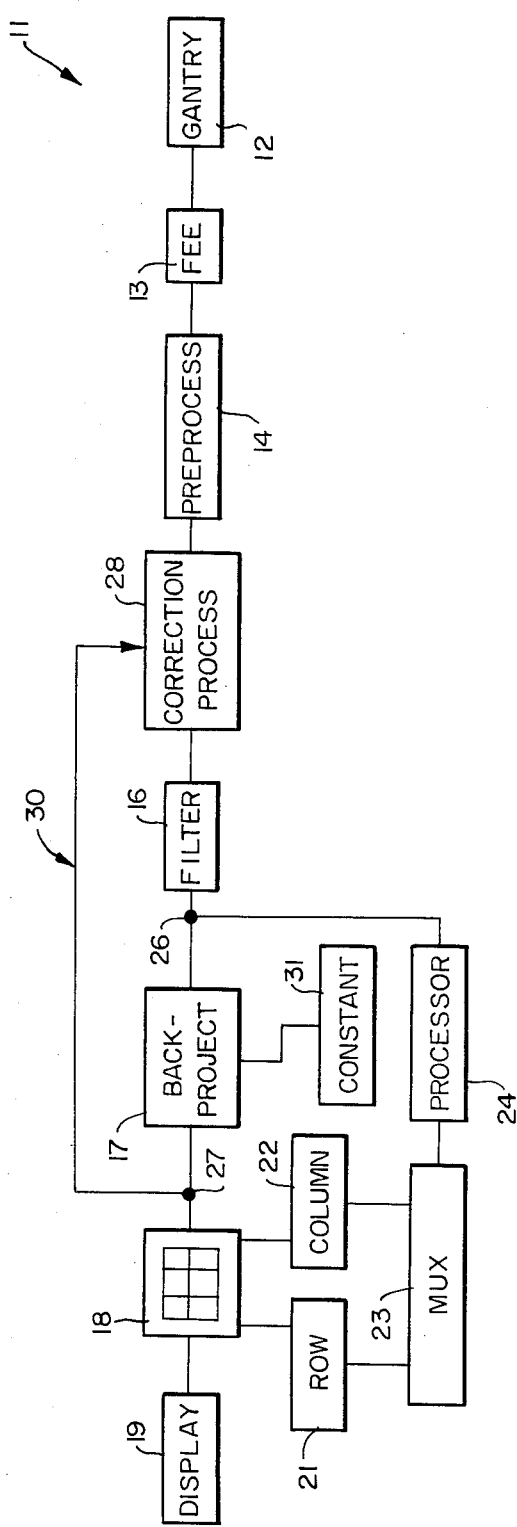
FIG. 1 is a block diagram showing an embodiment of a reprojection system used to correct polychromatic artifacts.

The CT Scanner system 11 of FIG. 1 comprises the gantry 12. The subject is exposed to radiation in the gantry 12 and the radiation is detected after traversing the subject. The detected signals are treated in the block 13 labelled FEE for Front End Electronics. The electrical signals are preprocessed by the processor 14. The output signals of 14 are called projections. The output of 14 is passed through to the correction unit 28. The unit performs a first-order polychromatic correction on the projections in order to generate the initial image.

The output of the correction unit 28 is passed to the filter 16. The filtered projections are backprojected by backprojector 17. The parameters used to control the backprojector are obtained from constant generator 31. The ouput of the backprojector is passed in the form of a digitized image in matrix 18. The matrix of digitized data is used to provide images on display device 19.

Means are provided for using the backprojector 17 to generate reprojections of the values in the matrix 18. More particularly row and column read out circuits 21 and 22 are shown coupled through multiplexer 23 which in turn is connected to the input of processor unit 24. Processor unit 24 is designed, in a preferred embodiment, to distinguish between data values of bone or soft tissue on a per matrix unit basis.

The output of unit 24 is connected via switch 26 to the backprojector 17. In the normal mode of image reconstruction, switch 26 is set so that the backprojector 17 uses the output of the filter 16 as its input. In the reprojection mode of the system, switch 26 is set so that the input to the backprojector 17 is provided by the output of unit 24.

The row and column data provided by units 21 and 22 are "backprojected" by unit 17 resulting in reprojections at switch 27. The constant generator 31 provides constants suitable for the operation of reprojection by the backprojector. Switch 27 is further used to pass the backprojected image to the matrix 18 in the normal mode of operation and to pass the reprojections to the correction unit 28 in the reprojection mode of the system.

Polychromatic error corrections are provided in the feedback loop 30 extending from the output of the backprojector 17 through the polychromatic error correction unit 28. In the polychromatic correction mode, the output of feedback loop 30 is combined with the output of unit 14 and then passed to the filter 16.

The sequence of operations required for backprojection, reprojection, and polychromatic correction is controlled by control unit, not shown, which is directly responsible for mode specification in units 23, 26, 27, 28, and 31.

To better explain the present system, a brief description of the mathematics of reprojection follows.

Consider the function f(x,y) which represents a reconstruction of a cross-section of an object and the path characterized with ($\theta$,t) given by:

$$t = x^* \cos(\theta) + y^* \sin(\theta), \quad (1)$$

where:

$$|t| < \infty,$$

and $$|\theta| < \pi/2.0.$$

Figure 2:
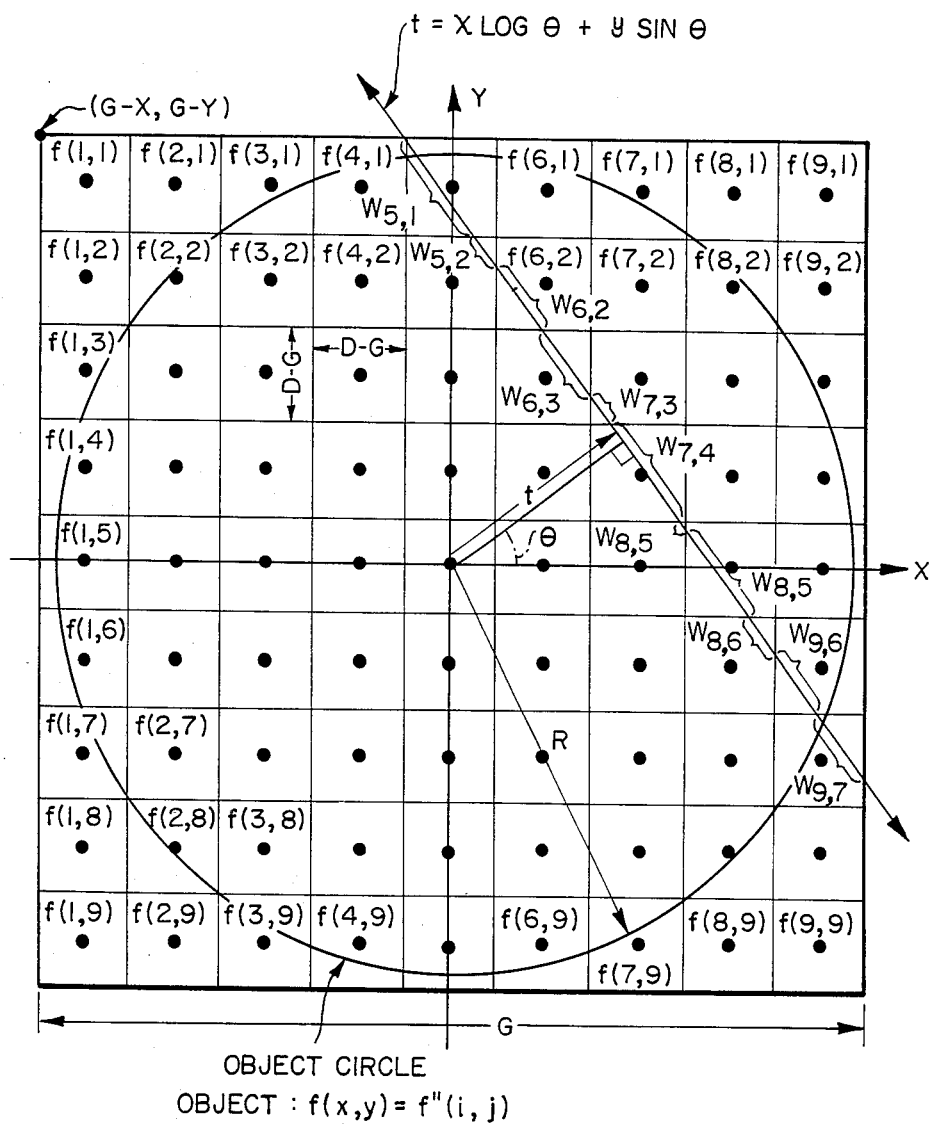
FIG. 2 demonstrates a ray traversing a digitized image.

The object and the path are depicted in FIG. 2.

A sample of the reprojection of f(x,y), along the path characterized by ($\theta$,t), p($\theta$,t), is given by:

$$p(\theta,t) = \int\int_{-\infty}^{\infty} f(x,y)\delta(t - x^*\cos(\theta) - y^*\sin(\theta))dxdy, \quad (2)$$

where $\delta(z)$ is a normal $\delta$ function described by:

$$\int_{-\infty}^{\infty} \delta(z)g(z)dz = g(0). \quad (3)$$

The integration in (2) is over strips of zero width. A strip of non-zero width can be incorporated into (2) by replacing the $\delta$ function with a normalized cross-section of the strip. The normalization ensures that the integral of the cross-section of the desired aperture function is unity.

The output of a reconstruction unit in an actual system is not as implied in (2). The result is actually a sampled representation of the function f(x,y). We denote the discrete version f''(i,j). This function is also depicted in FIG. 2. The indices for i and j are in the range [1,M]. One can easily show that f''(i,j) can be related to f(x,y) as follows:

$$f''(i,j) = f(x,y), \quad (4)$$

for $$x = GX (i-0.5)^* DG \quad (5)$$

$$y = GY (j-0.5)^* DG, \quad (6)$$

where $$DG = G/M. \quad (7)$$

The variables GX, GY, and G are defined in FIG. 2.

An approximate value of the reprojection, denoted p''($\theta$,t), can be found by substituting (4) into (2) and replacing the integrals with summations. The result is:

$$p''(\theta,t) = \sum_{i=1}^{M} \sum_{j=1}^{M} w(i,j;\theta,t)^* f''(i,j). \quad (8)$$

The function w(i,j; $\theta$,t) is the distance through the sample values of f''(i,j) for the line given by the parametric relationship ($\theta$,t). FIG. 2 depicts a situation in which the values of w(;) can be discerned. It is easy to incorporate strips of non-zero width into w(;). However, satisfactory reprojections and hence satisfactory polychromatic corrections have been obtained when zero width strips are used.

Now consider the generation of a reprojection value p''($\theta$,t), for the case when $$|\theta| < \pi/4.0, \tag{9}$$

Figure 3A:
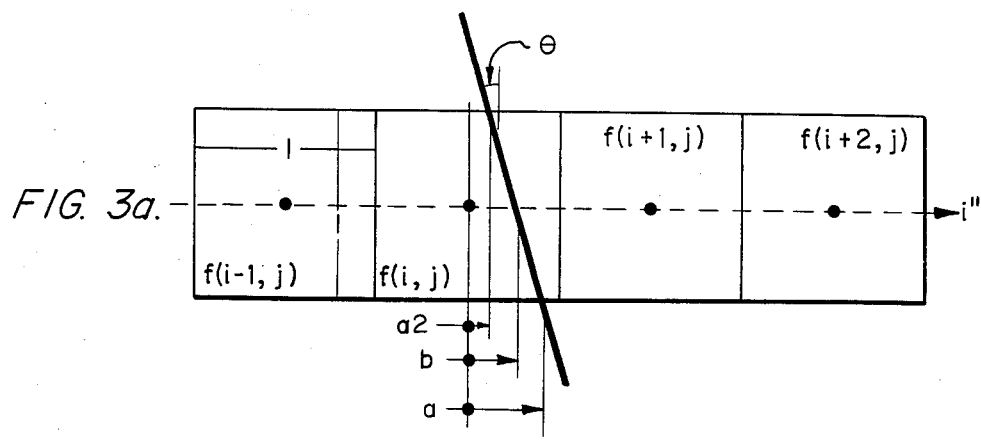
FIGS. 3a-c shows the three possible orientations of the ray of FIG. 2 crossing a row of the digitized image.
Figure 3B:
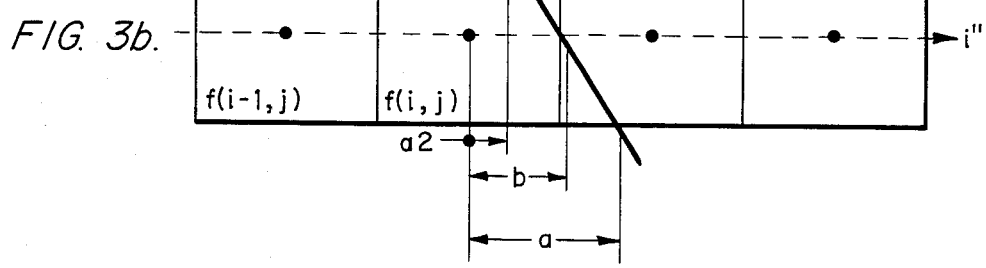
Figure 3C:
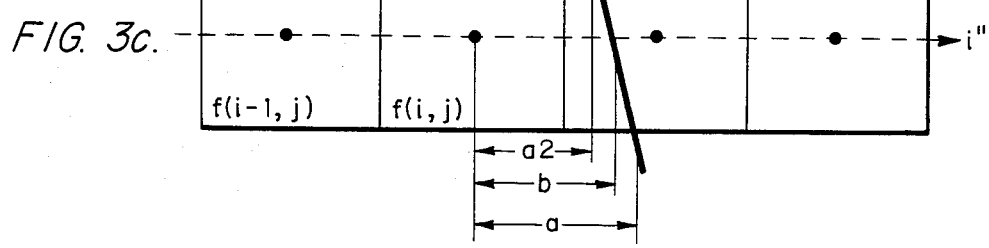

Now consider the intersection of the ray with the j'th row of the image. Assume that the ray intersects between the centers of pixels f''(i,j) and f''(i+1,j). Because of (9) only w(i,j; $\theta$,t) and w(i+1,j; $\theta$,t) can be non-zero. There are three cases for the two values of w(;). These cases are depicted in FIGS. 3a-c. Now the values of these two weight function samples in each of the three cases will be derived.

First solve for x in (1):

$$x = (t - y^* \sin(\theta))/\cos(\theta). \tag{10}$$

The value of y in (10) can be determined by evaluating (6) for the known value of j.

Now substitute (10) into (5) and solve for i. The result is:

$$i'' = (t/\cos(\theta) - y^* \tan(\theta) - \underline{GX} + 0.5^*\underline{DG})/\underline{DG}. \tag{11}$$

The variable i'' is used instead of 'i' in order to indicate that a continuous coordinate system is being used instead of an integer coordinate system implied by the index i.

The two pixels that contribute to the reprojection for the ray and from the j'th row are at indexes 'i' and i+1 where 'i' is given by:

$$i = \backslash i''/, \tag{12}$$

and $\backslash x/$ is the greatest integer less than or equal to x.

Now define the variable 'b' to be (see FIG. 3):

$$b = i'' - i \tag{13}$$

Let 'a' be the coordinate of the exit point of the ray with the bottom of the row. It is easy to show that it is given by:

$$a = b + 0.5^* \tan(\theta). \tag{14}$$

Let 'a2' be the coordinate where the ray enters the top of the row. It is given by:

$$a2 = b - 0.5^* \tan(\theta). \tag{15}$$

It is clear that the three cases depicted in FIGS. 3a-c can be described by using 'a' and 'a2'. The results are:

Case I:

$$a < 0.5 \text{ and } a2 < 0.5 \tag{16a}$$

Case II(a):

$$a > 0.5 \text{ and } a2 < 0.5, \theta > 0.0 \tag{16b}$$

Case II(b):

$$a < 0.5 \text{ and } a2 > 0.5, \theta < 0.0 \tag{16c}$$

Case III:

$$a > 0.5 \text{ and } a2 > 0.5. \tag{16d}$$

It can be shown that the weight functions are given by:

Case I:

$$w(i,j; \theta,t) = \underline{DG}/|\cos(\theta)| \tag{17a}$$

$$w(i+1,j; \theta,t) = 0 \tag{18a}$$

Case II(a): $\theta > 0.0$ $$w(i,j; \theta,t) = (0.5 - a2)^* \underline{DG}/|\sin(\theta)| \tag{17b}$$

$$w(i+1,j; \theta,t) = (a - 0.5)^* \underline{DG}/|\sin(\theta)| \tag{18b}$$

Case II(b): $\theta < 0.0$ $$w(i,j; \theta,t) = (0.5 - a)^* \underline{DG}/|\sin(\theta)| \tag{17c}$$

$$w(i+1,j; \theta,t) = (a2 - 0.5)^* \underline{DG}/|\sin(\theta)| \tag{18c}$$

Case III:

$$w(i,j; \theta,t) = 0 \tag{17d}$$
$$w(i+1,j; \theta,t) = \underline{DG}/|\cos(\theta)|. \tag{18d}$$

The contribution to the reprojection along the ray characterized by ($\theta$,t) by the j'th row is given by:

$$p''(\theta,t; j) = w(i,j; \theta,t)^* f''(i,j)$$
$$+ w(i+1,j; \theta,t)^* f''(i+1,j), \tag{19}$$

where 'j' in (19) indicates the contribution of the j'th row to the reprojection.

For a single ray, a method to calculate the reprojection along the ray that satisfies (9) is presented. The procedure is as follows:

[1] Loop through all M rows in the image.
[2] Calculate the y value of a row using (6).
[3] Calculate the intercept of the ray with the row using (11).
[4] Find i, b, a, and a2 using (12), (13), (14), and (15).
[5] Determine in which case the ray falls by using (16).
[6] For the specific cases, calculate the weights using (17) and (18).
[7] Update the reprojection sample using (19).
[8] Go to [1] if there are more rows to process.

In an actual reprojection system, all of the samples of a reprojection are desired. In theory, one could just use the above method for each of the samples in the reprojection. However, this procedure does not exploit the inherent similarity between the reprojection samples. The above method can be extended for the simultaneous calculation of all of the samples. Assume that N samples of a reprojection at an angle $\theta$ are desired. Also assume that the object is contained in a circle of radius R. The discrete samples of the reprojection can be given by:

$$p''(\theta,l) = p''(\theta,t(l)), \tag{20}$$

for
$$l = 1, 2, \ldots, N$$

$$t(l) = -R + (l - 0.5)^* \underline{DT}, \tag{21}$$

where $$\underline{DT} = 2.0^* R/N. \tag{22}$$

Assume that i'' has been calculated for a particular value of 'l'. Call this value i''(l). It can be seen from (11) and (21) that:

$$i''(l+1)=i''(l)+\underline{DT'},\qquad(23)$$

where $$\underline{DT'}=\underline{DT}/\cos(\theta)/\underline{DG}.\qquad(24)$$

Now assume that i''(l) has been calculated for the j'th row. This value is denoted by i''(l,j). One can show from (6) and (11) that i''(l,j) and i''(l,j+1) are related as follows:

$$i''(l,j+1)=i''(l,j)+\tan(\theta).\qquad(25)$$

A method that calculates all of the samples in a reprojection simultaneously can now be presented:
[1] Preset to zero all of the samples in the reprojection.
[2] Calculate cos ($\theta$), sin ($\theta$), and tan ($\theta$).
[3] Determine DT' with (24).
[4] Calculate i''(1,1) using (6), (11), and (21).
[5] Loop through all of the rows in the image.
[6] Loop through all of the reprojection samples.
[7] Find b, a, and a2 using (13), (14), and (15).
[8] Determine the weights using (16), (17), and (18).
[9] Update the projection sample with (19).
[10] Update i'' using (23).
[11] Go to [6] if there are more reprojection samples.
[12] Update i'' using (25).
[13] Go to [5] if there are more rows in the picture.

A normal backprojector operates by smearing a value of a filtered projection onto all of the pixels for a resulting image. The backprojector is given the index of the filtered projection that contributes to one of the four corner pixels in the image. The backprojector is also given increments of the indexes into the filtered projection for the pixels row- and column-adjacent to the corner pixel. From these three constants, the backprojector is able to calculate through, simple addition, the indexes of all of the pixels for a given filtered projection. Backprojectors are generally designed so that the number of projections, the number of samples per projection, the number of pixels in a row and a column of the image, and the physical size of the image can be variables. Thus a flexible co-processor is used in order to generate the constants required by the backprojector.

The above description of a backprojector directly applies to a parallel backprojection unit. With the proper choice of constants, a fan-beam backprojector also can be used as a parallel backprojector.

One can see that the above reprojection method can be implemented by backprojecting the M rows of the image as "projections", each containing M samples, resulting in a reconstructed "image", size N×1, representing the reprojection. The increment between sample values in a row of the resulting "image", is DT'. Because there is only one row in the "image", the column increment is not required by the backprojector. The initial value of i'' for each "projection" can be found using (11). The co-processor of the backprojector can be used to generate DT' and i'' thus allowing the backprojector to generate reprojections.

The only deviation of the above method from an exact backprojector implementation is the interpolation implied in steps [7] and [8]. An actual backprojector usually uses zero- or first-order interpolation between the two projection values when a ray crosses between projection sample values. The above method actually implies that a two-dimensional interpolation operation is required. The two variables in this interpolation scheme are the distance between the ray crossing and the left sample, b, and the angle of intersection, $\theta$. It is easy to see that an actual backprojector could be modified to incorporate this new exact interpolation scheme.

Assume that along a row in an image, the object function is a slowly varying function. Then, to a first-order approximation, zero- or first-order interpolation between the two samples that a ray crosses will be sufficient. If we make this assumption, then the above method (with [7] and [8] replaced with linear interpolation) is a description of an actual backprojector. (Note that the resulting reprojections are scaled by known factors.)

Thus, with linear interpolation and scaling with known factors, the weights for the back-projector to provide pseudo projections, are by way of example:

$$W(i,j;\theta,t)=(l-b)*\underline{DG}/|\cos\theta|\qquad(17e)$$

$$W(i+1,j;\theta,t)=b*\underline{DG}/|\cos\theta|\qquad(18e)$$

Now return to the assumption presented in (9). This assumption was needed so that a ray crosses, at most, two samples in a row. The method presented above works only for values of $\theta$ that satisfy this assumption. For values of $\theta$ that do not fall in this range, the "projections" given to the backprojector are not the rows of the image but the columns of the image.

Thus, when calculating reprojections for many angles, one has to divide the values of $\theta$ in two categories: I: those values of $\theta$ that satisfy (9); and II: those that do not satisfy (9).

A universal reprojection generation method can now be presented:
[1] Use the normal reprojection method for category I.
[2] Rotate the image by 90 degrees.
[3] Use the normal reprojection method for category II.

This system enables an unmodified backprojector to be used to obtain reprojections. The advantage of this system is that it takes advantage of the fact that backprojectors are designed to exploit the parallelism in the backprojection algorithm. Thus the time required to obtain reprojections is reduced sufficiently so that this system can be used for clinically viable artifact correction.

While the principles of the invention have been explained in connection with specific methods and equipment, it should be understood that the disclosure has been made by way of example only. Numerous changes can be made to the example given without departing from the spirit and scope of the invention as defined in the accompanying claims.

What is claimed is:

1. A post-reconstruction artifact correction system for computerized tomography (CT) images reconstructed by back-projection, said system comprising:
   (a) detector means for converting radiation obtained from source means at different angular positions relative to a subject to electrical signals, said radiation passing through said subject in straight line rays from said source means to said detector means, said different angular positions defining an object circle;
   (b) means for preprocessing said electrical signals to provide projections indicative of absorption of the radiation in each of said rays;
   (c) means for filtering said projections;

(d) back-projector means for converting said filtered projections to digitized original image data;
(e) memory matrix means for storing said digitized image data in elemental matrix areas;
(f) means for reading out said digitized original image data from said elemental matrix areas;
(g) means for processing the read-out data to obtain spectral components of said read-out data;
(h) means comprising said back-projector means for converting the spectral components of the digitized original image data into reprojections;
(i) said means for converting the spectral components comprising means for transmitting the spectral components to the input of said back-projector means and receiving said reprojections at the output of said back-projector means;
(j) means for combining said reprojections with said projections to obtain error projections;
(k) means including said back-projector means for converting said error projections to digitized error image error data; and
(l) means for combining the error image data and the original data to obtain error free data for providing an image substantially free of spectral artifacts.

2. The system of claim 1 wherein said means for obtaining spectral component comprises means for separating the stored image data into bone data and soft tissue data, whereby said reprojections comprise first reprojections which are generated from the bone data and second reprojections generated from the soft tissue data, means for combining said first and second reprojections and said projections to provide error projections, means for filtering said error projections, and means for reconstructing the image using said back-projector and filtered error projections.

3. The system of claim 1 wherein said back-projector means include constant generating means for providing constants to said back projector means, said constant generating means providing a first set of constants to said back-projector means for use in converting projections into digitized image data and a second set of constants for use in converting digitized image data into reprojections.

4. The system of claim 1 wherein the image contains "M" rows of "M" columns each, said back-projector means operates to provide reprojections based on said rays through said image, each of said rows contributing a value $p''(\theta,t;j)$ based on a weight factor $w(i,j;\theta,t)$ to said reprojections of said ray intercepting the row according to the following equation:

$$p''(\theta,t;j) = w(i,j;\theta,t)*f''(i,j) + w(i+1,j;\theta,t)*f''(i+1,j)$$

with $$w(i,j;\theta,t) = (1-b)*\underline{DG}/|\cos\theta|,$$

and $$w(i+1,j;\theta,t) = b*\underline{DG}/|\cos\theta|$$

where:
p'' is the contribution to the reprojection along the ray defined by the parameteric values $(\theta,t)$,
t is the normal to the ray from the center of the object circle, and
$\theta$ is the angle of t to the horizontal,
j is the row designation,
i is the column designation,
f''(i,j) is the discrete version of the elemental matrix area making up the cross section of the subject defined by the function,
f(x,y) where $$f''(i,j) = f(x,y)$$

for:

$$x = \underline{Gx} + (i-0.5)*\underline{DG},$$

$y = \underline{Gy} - (j-0.5)*\underline{DG}$ ($\underline{DG}$ = the width and height of an elemental area), $w(i,j;\theta,t)$ is the weight factor used by the back-projector operating with linear interpolation for the elemental area having the value f''(i,j).

5. The system of claim 4 wherein means are provided for rotating the image by 90° prior to reading out the image when $\theta$ is greater than $\pi/4$.

6. The system of claim 4 including means for determining all of the reprojections for each angular position simultaneously said means for determining all of the reprojections for each angular position comprises:
(a) means for calculating $\cos\theta$, $\sin\theta$ and $\tan\theta$, for each angular position;
(b) means for determining a value DT',
where:

$$DT' = \underline{DT}/\cos\theta/\underline{DG'}$$

where DT is the diameter of the object circle divided by the number of samples N per reprojection;
(c) means for repeating for each row of the image and each sample of the reprojection;
(d) means for finding the values for b,
where:

$$b = i'' - |i''|$$

with, $|i''|$ = the greatest integer less than or equal to i'';
(e) means for determining the weights $w(i,j;\theta,t)$, using:

$$w(i,j;\theta,t) = (1-b)*\underline{DG}/|\cos\theta|,$$

$$w(i+1,j;\theta,t) = b*\underline{DG}/|\cos\theta|;$$

(f) means for updating the reprojection p''(o,t;j) using:

$$p''(o,t;j) = w(i,j;\theta,t)*f''(i,j) + w(i+1,j;\theta,t)*f''(i+1,j);$$

(g) means for updating the intercept using $$i''(l+1) = i''(l) + DT',$$

where:

$$DT' = \underline{DT}/\cos\theta/\underline{DG};$$

(h) means for repeating for all samples;
(i) means for further updating i'' using equation:

$$i''(l,j+1) = i''(l,j) + \tan\theta;$$

and
(j) means for repeating for all rows.

7. The system of claim 6 wherein means are provided for rotating the image by 90° prior to reading out the image when $\theta$ is greater than $\pi/4$.

8. A post-reconstruction artifact correction method for reducing artifacts in images that were reconstructed by back-projecting to obtain the image data arranged in rows and columns from projections, the method comprising the steps of:

(a) transferring the image data into the input of the back-projector, supplying constants to the back-projector to cause the back-projector to generate reprojections, said constants including the angle of a path through the image, the length of an elemental area of the image; and the point of intersection of the path with said rows; and (b) obtaining the reprojections at the output of the back-projector;

(c) said method further comprising:

(1) transferring either the rows or the columns of the image as projections to the input of the back-projector;

(2) invoking the backprojector to reconstruct an output image with only one row;

(3) providing increments between sample values of the one row in the output of the backprojector, said increments being related to the distance between samples and the angle of the samples in the reprojection; and (4) providing initial row values related to the angle of the samples and the orientation of the image.

9. The method of claim 8 wherein rows are transferred if the angle of the samples of the reprojection has an absolute value between zero and 45 degrees; otherwise, columns are transferred for all other angles.

* * * * *